(12) United States Patent
Burkholz et al.

(10) Patent No.: US 10,806,901 B2
(45) Date of Patent: Oct. 20, 2020

(54) CATHETER ADAPTER WITH DISTAL INNER DIAMETER CURVATURE PROVIDING KINK RESISTANCE

(71) Applicant: Becton, Dickinson and Company, Franklin Lakes, NJ (US)

(72) Inventors: Jonathan Karl Burkholz, Salt Lake City, UT (US); Jeffrey C. O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 251 days.

(21) Appl. No.: 15/285,601

(22) Filed: Oct. 5, 2016

(65) Prior Publication Data

US 2017/0120008 A1 May 4, 2017

Related U.S. Application Data

(60) Provisional application No. 62/247,264, filed on Oct. 28, 2015.

(51) Int. Cl.
*A61M 25/06* (2006.01)
*A61M 25/00* (2006.01)
*A61M 39/06* (2006.01)

(52) U.S. Cl.
CPC .... *A61M 25/0606* (2013.01); *A61M 25/0023* (2013.01); *A61M 25/0067* (2013.01); *A61M 25/0097* (2013.01); *A61M 39/06* (2013.01); *A61M 2025/0059* (2013.01); *A61M 2025/0098* (2013.01); *A61M 2039/062* (2013.01)

(58) Field of Classification Search
CPC .......... A61M 25/0606; A61M 25/0023; A61M 25/0067; A61M 25/0097

USPC ........................................................ 604/523
See application file for complete search history.

(56) References Cited

U.S. PATENT DOCUMENTS

| | | | |
|---|---|---|---|
| 4,068,660 A | | 1/1978 | Beck |
| 4,311,137 A | * | 1/1982 | Gerard ............ A61M 25/0606 604/122 |
| 2009/0157007 A1 | | 6/2009 | McKinnon |
| 2009/0192496 A1 | * | 7/2009 | Suwito ............ A61M 25/0097 604/533 |
| 2011/0009831 A1 | | 1/2011 | Burkholz et al. |

FOREIGN PATENT DOCUMENTS

| | | |
|---|---|---|
| JP | 2011506042 A | 3/2011 |
| JP | 2011510744 A | 4/2011 |
| WO | 9944654 A1 | 9/1999 |
| WO | 2015133281 A1 | 9/2015 |
| WO | 2014134248 A1 | 9/2017 |

OTHER PUBLICATIONS

PCT International Preliminary Report on Patentability in PCT/US2016/055669 dated May 11, 2018, 7 pages.
PCT International Search Report and Written Opinion in PCT/US2016/055669 dated Jan. 13, 2017, 11 pages.

* cited by examiner

*Primary Examiner* — Phillip A Gray
(74) *Attorney, Agent, or Firm* — Servilla Whitney LLC (57) ABSTRACT

Catheter adapters and vascular access device including catheter adapters are discloses. The catheter adapter tip opening has an internal curvature defining a tapered region in the lower portion, but not the upper portion, to support a flexured portion of the catheter to prevent kinking and occlusion.

31 Claims, 7 Drawing Sheets

CATHETER ADAPTER WITH DISTAL INNER DIAMETER CURVATURE PROVIDING KINK RESISTANCE

CROSS-REFERENCE TO RELATED APPLICATIONS

This application claims priority under 35 U.S.C. § 119(e) to U.S. Provisional Application No. 62/247,264, filed Oct. 28, 2015, the disclosures of which are incorporated herein by reference in their entirety.

TECHNICAL FIELD

Aspects of the present disclosure relate to an adapter having a catheter adapter tip opening with an internal curvature to support the tubular catheter as it transitions from the catheter adapter to a patient's vein to prevent catheter kinking and occlusion, and also vascular access devices including catheter adapters.

BACKGROUND

Infusion therapy using catheters to administer fluids into and drain fluids out of the body has been a standard practice in medical procedures for years. Patients in a variety of settings including in hospitals, in home care, and other patients receive fluids, pharmaceuticals, and blood products via a vascular access device inserted into a patient's vascular system. Catheters of various types and sizes have been used extensively by physicians in a variety of procedures including, but not limited to, treating an infection, providing anesthesia or analgesia, providing nutritional support, treating cancerous growths, maintaining blood pressure and heart rhythm, and many other clinically significant uses. However, catheter occlusion is a frequent complication experienced when using catheters in medical procedures and treatment. Catheter kinking results in a reduction of fluid volume delivery rate and, in many cases, causes a fluid stoppage and a rupture of the catheter wall with an accompanying loss of fluid.

Intravenous therapy is facilitated by vascular access devices located outside the vascular system of a patient (extravascular devices). Extravascular devices that may access a patient's peripheral or central vasculature, either directly or indirectly include closed access devices, such as the BD Q-SYTE™ closed luer access device of Becton, Dickinson and Company; syringes; split-septum devices; catheters; and intravenous (IV) fluid chambers. A vascular device may be indwelling for short term (days), moderate term (weeks), or long term (months to years). A vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter is commonly incorporated into a catheter adapter to aid in the ease of use, accessibility and utility of the catheter. A catheter adapter is generally a rigid, plastic, tubular member adapted to house one end of the catheter such that one end of the catheter is supported by the catheter adapter and the body and tip of the catheter extends beyond a first end of the catheter adapter. A catheter adapter generally further includes a second end adapted to receive additional infusion components for use with the catheter. For example, the second end of a catheter adapter may include a set of threads for attaching an intravenous line or for coupling a syringe to the catheter adapter thereby providing access to the patient's vasculature via the attached catheter.

The catheter may be inserted transcutaneously. When inserted transcutaneously, the insertion of the catheter is commonly aided by an introducer needle. The introducer needle is commonly housed inside the lumen of the catheter such that the gauge of the needle approximates the inner diameter of the catheter. The needle is positioned within the catheter such that the needle tip extends beyond the tip of the catheter whereby the needle is used to penetrate the patient's vein and provide an opening for insertion of the catheter.

During insertion into a patient, the needle and catheter generally approach the patient's vein at an angle of about 30° wherein the needle initially punctures the patient's epidermis and then continues into the vein. Once the needle and catheter tip enter the patient's vein, the needle and catheter are then repositioned so that the needle and catheter are brought into a position generally parallel with the patient's vein so that the needle and catheter may be inserted into the lumen of the patient's vein. When the catheter has been properly positioned within the patient's vein, the needle is removed from the lumen of the catheter and the catheter adapter is secured to the patient to prevent premature removal of the catheter.

Typically the catheter adapter is secured to the patient by fastening the catheter adapter to the patient's skin via tape, a securement device and/or a securement dressing. When securing the catheter adapter to the patient's skin, the root region of the catheter immediately exiting the catheter adapter must arch to accommodate the catheter's transition from the generally parallel, secured orientation of the catheter adapter, to the insertion angle of the catheter; an angle of approximately 30°.

General practice provides that the catheter be inserted into a patient such that an extended section of catheter is left between the patient and the catheter adapter to allow for transitional arching of the catheter. This exposed, archable length of catheter biases the catheter towards the patient's skin and thus the root region of the catheter experiences leverage forces because the catheter acts as a lever and the first end of the catheter adapter acts as a fulcrum exerting an upward force on the root region of the catheter. This upward force of the first end of the catheter adapter is undesirable due to the likelihood of occlusion of the root region of the catheter against the more rigid catheter adapter. Occlusion typically occurs as the patient and or the catheter is moved, increasing the angle of insertion in relation to the fixed position of the catheter adapter. For example, if the repositioning of the catheter and/or patient causes the catheter to be inserted further into the patient, the archable length of catheter between the patient and the catheter adapter decreases, which increases the angle of insertion and the upward force of the immobilized catheter adapter on the root region of the catheter. As the angle of insertion increases, the upward force of the catheter adapter also increases until the structural rigidity of the catheter wall is overcome, causing the catheter to kink.

Occlusion of the catheter is undesirable because occlusions slow or stop the flow through the catheter, creating undesirable backpressures that may cause the infusion system to malfunction and/or be damaged. Furthermore, occlusions reduce the efficiency of the infusion system, which could negatively affect treatment of the patient or the diagnostic procedure. Moreover, the exposed arched catheter section may become contaminated and pose a health risk to the patient. For example, an exposed section of catheter may become contaminated and then inserted into the patient as the patient and/or catheter is readjusted due to normal use by the patient and/or clinician. To reduce the likelihood of contamination and subsequent exposure to the patient, clinicians seek to minimize the length of exposed catheter by initially over-inserting the catheter into the patient. By reducing the length of exposed catheter, the upward force of the first end of the catheter adapter is increased, increasing the likelihood of occlusion within the root region of the catheter.

Contamination of the catheter and/or patient is undesirable for obvious reasons, the most obvious being that contamination may lead to secondary infection and/or complications unanticipated by the treating physician. Furthermore, a contaminated catheter may introduce a virus and/or bacteria to the patient that may conflict with the patient's primary therapy such that the patient is unable to receive further needed treatment.

Therefore, kink-resistant catheter adapters which can support catheters are desirable because they can reduce the possibility of occlusions and maintain a minimum fluid volume delivery rate. Although various attempts have been made to provide vascular access devices with a kink resistant catheter, there is still a need to provide a vascular access device that reduces the susceptibility of the catheter to kinking when flexed or bent during fluid delivery. It would also be desirable to provide a kink resistant catheter adapter that increases ease of penetration into a patient's vein, while providing the benefit of maintaining patency and flow rates throughout the life of the device. There is also a need for a vascular access device that allows for a steeper insertion angle which can be useful for subcutaneous injection as it supports the catheter as it is secured flat against the skin after a steep insertion.

SUMMARY

A first embodiment pertains to a vascular access device comprising a catheter including a flexured portion, a catheter adapter having a distal end and a proximal end with an overall length extending from the distal end to the proximal end, an internal cavity, an upper portion, a lower portion, a distal tip having a catheter adapter tip opening having a circumference and through which the catheter extends, the catheter adapter tip opening having an internal curvature defining a tapered region in the lower portion. The tapered region supports the flexured portion of the catheter to provide an angle of insertion for the catheter without restricting a flow through the catheter. The tapered region provides conical relief to the catheter. The overall length is substantially equivalent at the upper portion and the lower portion, and the tapered region is less than the overall length.

In one embodiment, the internal curvature of the lower portion of the catheter adapter tip opening defines a chamfer. In yet another embodiment, the internal curvature of the lower portion of the catheter adapter tip opening is either rounded or trumpet shaped.

In one or more embodiments, the lower portion of the catheter adapter tip opening defines a radius at the distal tip that incrementally decreases moving away from the distal tip. In one or more embodiments, the upper portion of the catheter adapter tip opening does not include an internal curvature extending from the distal tip.

The vascular access device may be a central venous catheter, a peripherally inserted central catheter, a peripheral intravenous cannula, an arterial catheter, or a mid-line catheter.

A portion of the catheter is housed within the internal cavity of the catheter adapter. The catheter is fixedly attached to the catheter adapter.

In one embodiment, the angle of insertion is within a range of about 1° to about 60°. In a specific embodiment, the angle of insertion is about 15-45°.

In one embodiment, a radius of the upper portion is asymmetrical in relation to the radius of the lower portion. In another embodiment, the upper portion of the catheter adapter is oriented tangentially to the catheter.

In one embodiment, the internal curvature in the lower portion of the adapter extends across a portion of a circumference of catheter adapter tip opening and defines an arc forming an angle in a range of 90° to 360°. In a specific embodiment, the angle is in the range of 180° to 360°.

The vascular access device further comprises an introducer needle in the internal cavity, the needle having a distal end a proximal end and a needle hub connected to the proximal end of the introducer needle.

The vascular access device further comprises an extension tube extending from the catheter adapter and in fluid communication with the internal cavity of the catheter adapter, at least one at of a luer access, a blood control septum, an air vent and a notch in the introducer needle.

In one embodiment, the vascular access device further comprises a wing element extending radially outward from the catheter adapter. The wing element comprises a first wing member extending from one side of the catheter adapter. In yet another embodiment, the wing element further comprises a second wing member extending opposite the one side of the catheter adapter.

In one embodiment, at least a portion of the catheter adapter is made from a first material and at least a portion of the distal tip is made from a second material that is more flexible than the first material. In yet another embodiment, at least a majority of the catheter adapter is made from a first material and at least a portion of the distal tip is made from a second material that is more flexible than the first material. In one or more embodiments, the distal tip includes a flexible, kink resistant extension extending from the catheter adapter tip opening to provide support for the catheter.

In one embodiment, the needle further includes a bevel on the distal tip and the bevel of the needle is oriented in an asymmetrical orientation in relation to the conical relief.

In one or more embodiments, the upper portion is absent a catheter adapter tip opening having an internal curvature defining a tapered region.

Another aspect of the disclosure pertains to an apparatus for preventing a restricted flow within a catheter. In one embodiment, the apparatus comprises a catheter adapter having a distal end and a proximal end with an overall length extending from the distal end to the proximal end, an internal cavity, an upper portion, a lower portion and a distal tip having a catheter adapter tip opening through which a catheter including a flexured portion extends. The overall length is substantially equivalent at the upper portion and the lower portion. The lower portion of the adapter has a curved surface to support the flexured portion of the catheter at a desired angle of insertion into a patient and to prevent kinking of the catheter. In one or more embodiments, the upper portion of the adapter in contact with the catheter has a substantially straight surface and constant thickness to maintain rigidity of the catheter during insertion of the catheter into a patient.

In one or more embodiments, the upper portion of the catheter adapter tip opening defines in cross section a semicircular arc forming an angle in a range of 0° to 270° and the lower portion of the catheter adapter tip opening defines in cross section a partial ellipse. In one or more embodiments, the lower portion of the catheter adapter tip opening forms an angle in a range of 0° to 270.

DETAILED DESCRIPTION

Before describing several exemplary embodiments of the disclosure, it is to be understood that the description provided is not limited to the details of construction or process steps set forth in the following description. The devices described herein are capable of other embodiments and of being practiced or being carried out in various ways.

In this disclosure, a convention is followed wherein the distal end of the device is the end closest to a patient and the proximal end of the device is the end away from the patient and closest to a practitioner.

The disclosure describes various embodiments of a catheter adapter, which may be used in combination with other components such as a needle hub assembly including a needle to provide various vascular access devices. Vascular access devices according to one or more embodiments include but are not limited to central venous catheters, peripheral inserted central catheters, peripheral intravenous cannulas, arterial catheters, and mid-line catheters.

Figure 5:
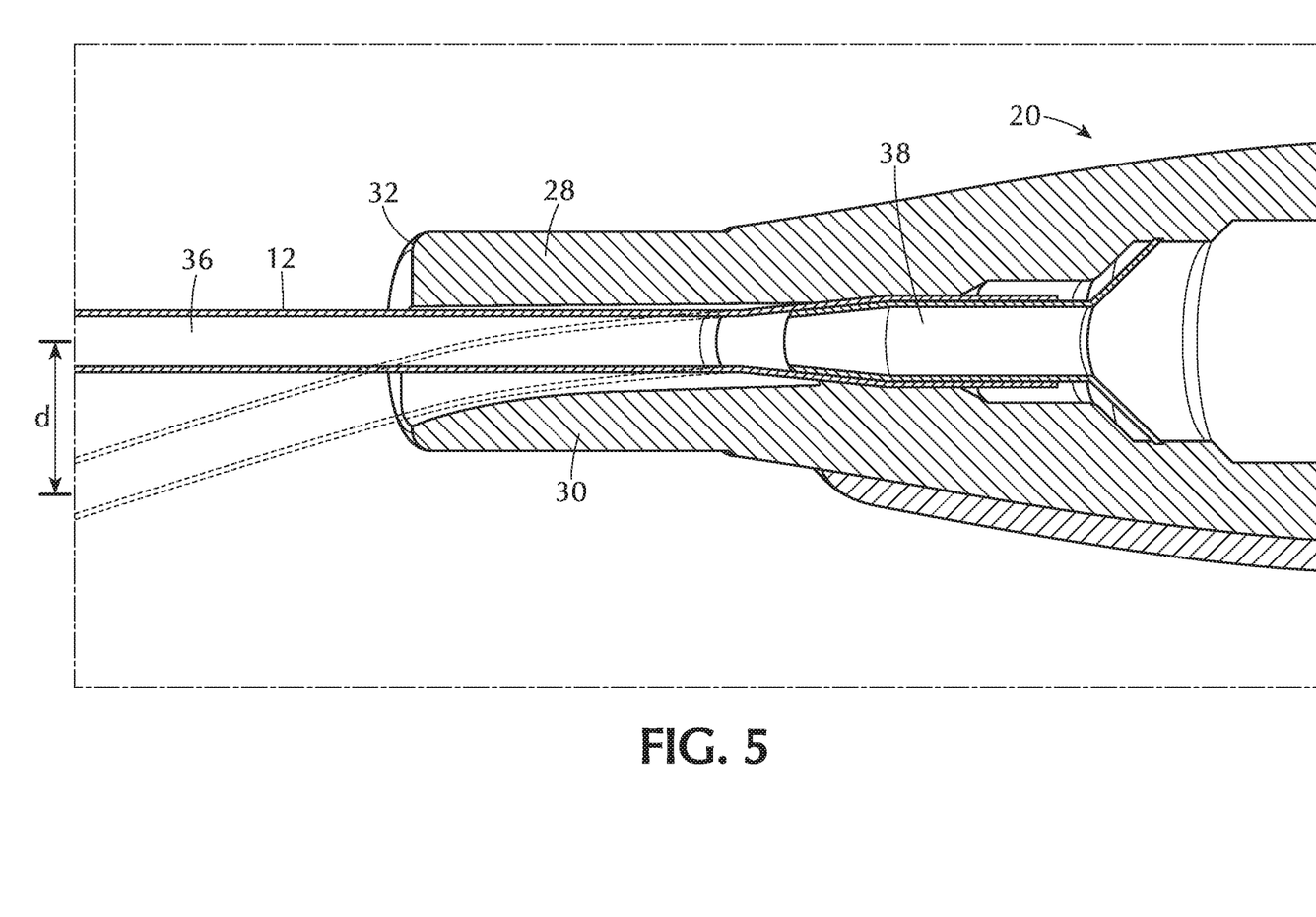
FIG. 5 is a partial cross-sectional view of a catheter adapter including a chamfered opening.
Figure 6A:
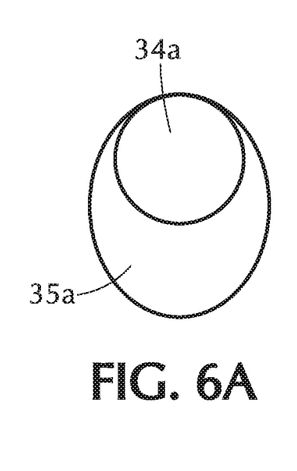
FIG. 6A illustrates a cross-section profile of a catheter adapter tip according to an embodiment.
Figure 6B:
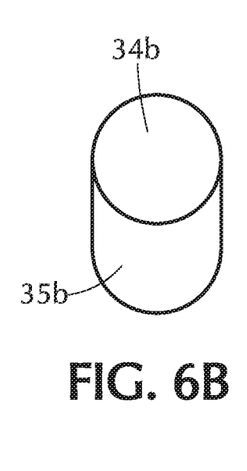
FIG. 6B illustrates a cross-section profile of a catheter adapter tip according to an embodiment.
Figure 6C:
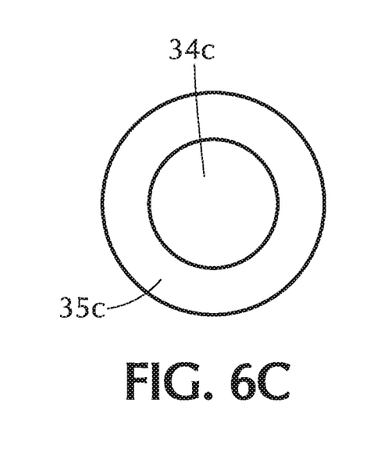
FIG. 6C illustrates a cross-section profile of a catheter adapter tip according to an embodiment.
Figure 7:
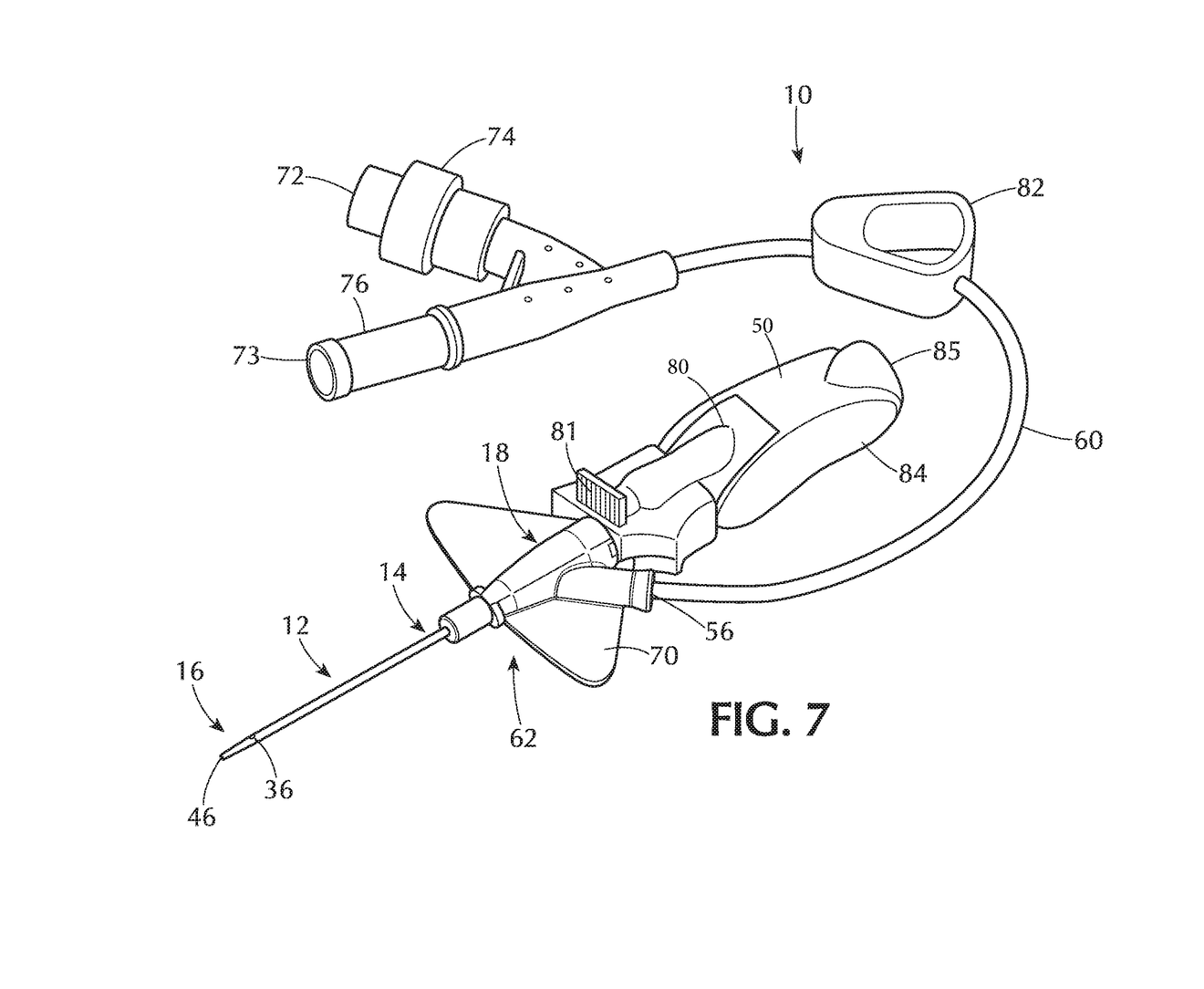
FIG. 7 is a perspective view of one or more embodiments of a vascular access device including catheter adapter according to an embodiment.

Referring to the drawings in which like reference characters refer to like parts throughout the several views thereof, FIGS. 1-6 illustrates a catheter adapter 20 and FIG. 7 illustrates a non-limiting example of a vascular access device 10 utilizing a catheter adapter in accordance with one or more embodiments of the present disclosure.

Figure 1:
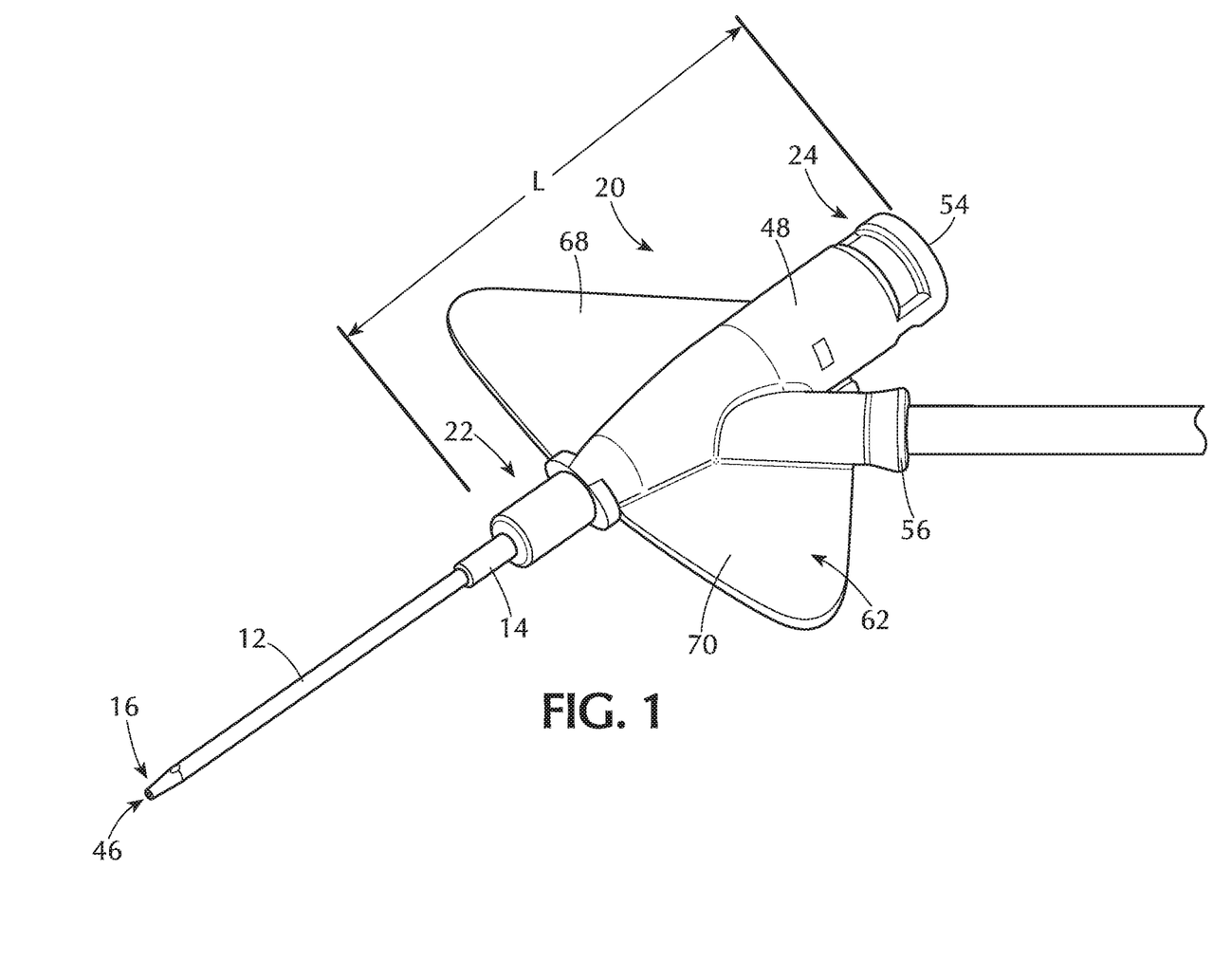
FIG. 1 illustrates a perspective view of a catheter adapter according to a first embodiment.
Figure 2:
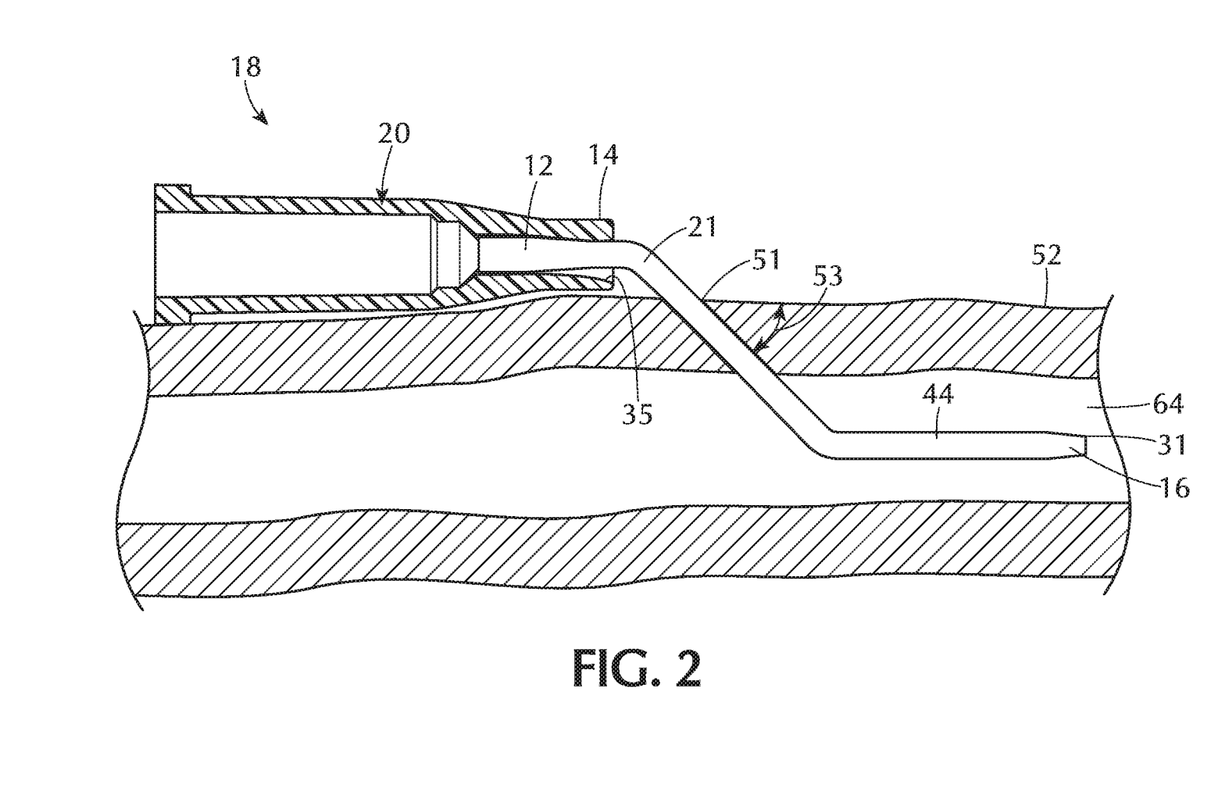
FIG. 2 is a partial cross-section view of an embodiment of a vascular access device wherein a catheter of the device is inserted in a patient.
Figure 3:
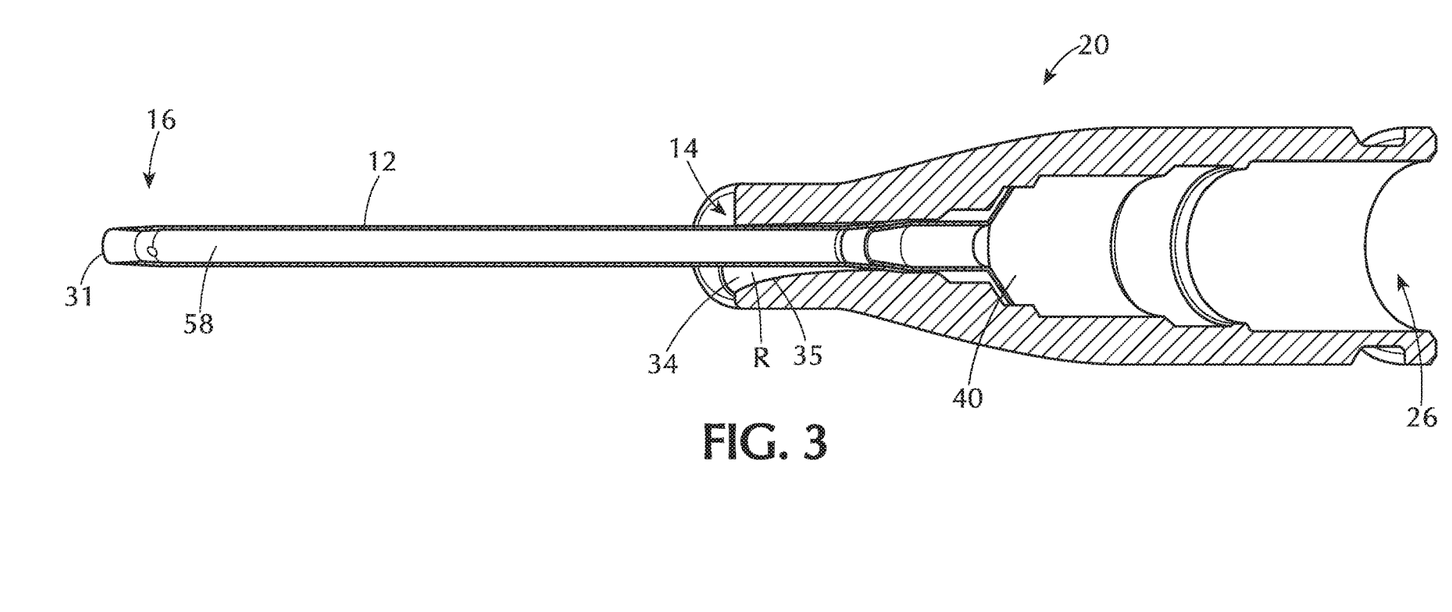
FIG. 3 is a cross-sectional view of a catheter adapter including a chamfered opening.

As shown in FIGS. 1-5, catheter adapter 20, which can be assembled with a hub assembly as described further below with respect to FIG. 7, includes a catheter 12 having a proximal end 14, a distal end 16 and flexured portion 21, a catheter adapter 20 having a distal end 22 and a proximal end 24, an internal cavity 26, an upper portion 28, a lower portion 30 and an adapter tip 32 having a catheter adapter tip opening 34 having a circumference through which the catheter 12 extends. As shown in FIGS. 2 and 3, the catheter adapter 20 is connected to the proximal end 14 of the catheter 12. The catheter adapter 20 extends from the adapter tip 32 to the proximal end 24 defining a catheter adapter length "L". An introducer needle 36 extends through the catheter 12. A needle hub 40 is connected to the proximal end 38 of the introducer needle 36.

As shown in FIGS. 2-5, the overall length L of the catheter adapter is substantially equivalent at the upper portion and the lower portion, and the catheter adapter tip opening 34 has an internal curvature defining a tapered region at surface 35 in the lower portion of the catheter adapter but not the upper portion of the catheter adapter, wherein the tapered region at surface 35 supports the flexured portion of the catheter to provide an angle of insertion for the catheter without restricting a flow through the catheter, the tapered region being less than the overall length. The internal curvature at surface 35 of the lower portion of the catheter adapter tip opening 34 defines a chamfer.

As best seen in FIG. 3, the lower portion of the catheter adapter tip opening 34 defines a radius "R" at the distal tip that incrementally decreases moving away from the distal tip in a proximal direction. In other words, since the lower portion of the catheter adapter tip 34 has surface 35, the radius R will be larger at the distal most portion of the tip than the radius measured at locations located a distance away from the tip in a proximal direction. Thus, the radius R continually decreases as the radius of the opening is measured at locations that are further away from the adapter tip 32 in a proximal direction. In one or more embodiments, the upper portion of the catheter adapter tip opening 34 does not include an internal curvature extending from the distal tip. The radius of the upper portion may be asymmetrical in relation to the radius of the lower portion. In one or more embodiments, the upper portion of the catheter adapter is oriented tangentially to the catheter.

Figure 4:
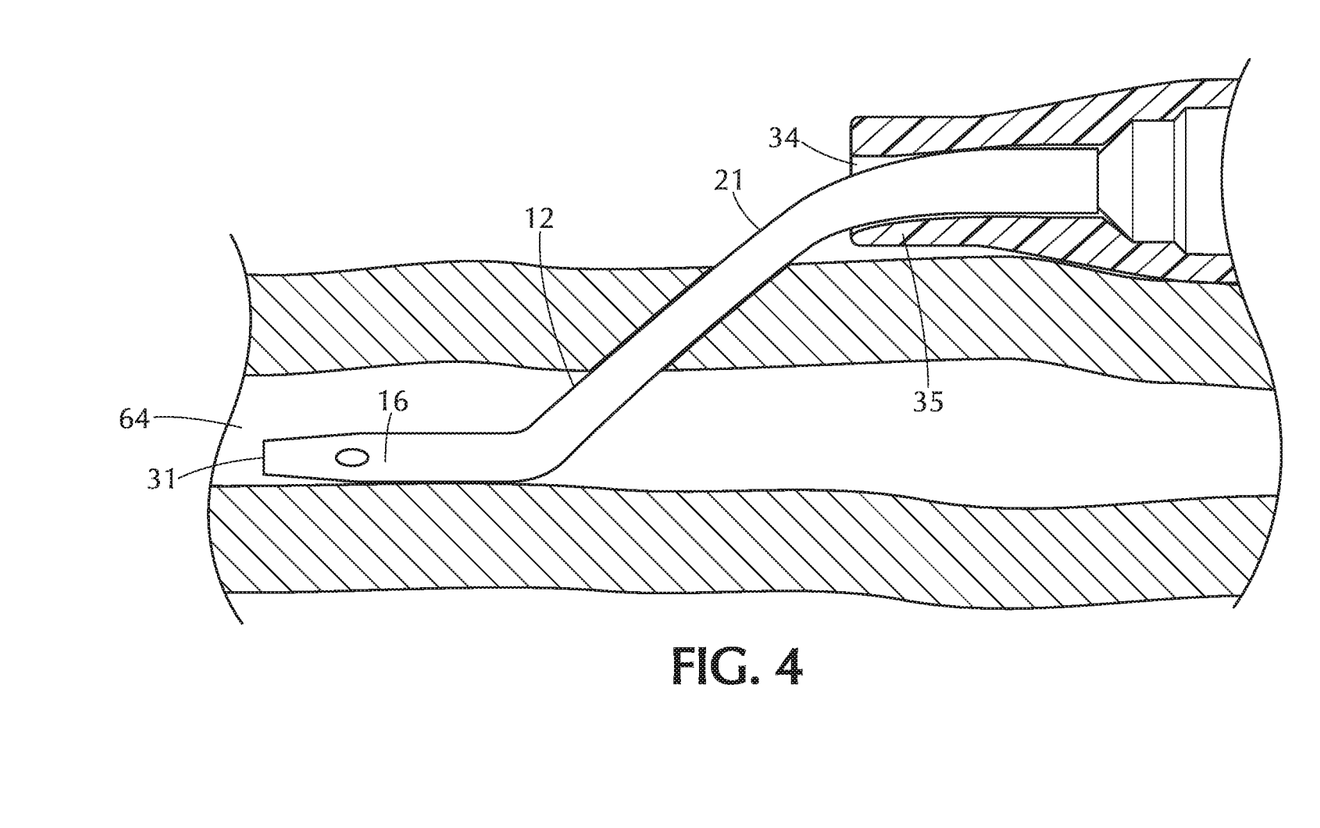
FIG. 4 is a partial cross-section view of an embodiment of a vascular access device wherein a catheter of the device is inserted in a patient and a catheter adapter tip is contoured on a lower portion.

As shown in FIGS. 3-5, in one or more embodiments, the internal curvature at surface 35 of the lower portion of the catheter adapter tip opening 34 defines a chamfer. In yet another embodiment, the internal curvature at surface 35 of the lower portion of the catheter adapter tip opening 34 is rounded or trumpet shaped. In one or more embodiments, the internal curvature at surface 35 in the lower portion of the adapter extends across a portion of the circumference of catheter adapter tip opening 34 and defines an arc forming an angle in the range of 90° to 270°. In a specific embodiment, the angle is in the range of 180° to 270°.

In one or more embodiments, the catheter adapter 18 can be a part of an apparatus for preventing a restricted flow within a catheter 12 including a catheter adapter 18 as described above having a distal end 22, a proximal end 24, an overall length L extending from the distal end to the proximal end, an internal cavity 26, an upper portion 28, a lower portion 30 and a distal tip 32 having a catheter adapter tip opening 34 through which a catheter including a flexured portion 21 extends, wherein the overall length is substantially equivalent at the upper portion and the lower portion, the lower portion of the adapter has a curved surface to support the flexured portion of the catheter at a desired angle of insertion into a patient and to prevent kinking of the catheter, the upper portion of the adapter in contact with the catheter 12 having a substantially straight surface and constant thickness to maintain rigidity of the catheter during insertion of the catheter into a patient. In one or more embodiments, the upper portion of the catheter adapter tip opening 34 defines in cross section a semicircular arc forming an angle in the range of 90° to 180°. In one or more embodiments, the lower portion of the catheter adapter tip opening 34 defines in cross section a partial ellipse.

Catheter 12 is generally tubular and flexible comprising a shaft of uniform thickness having a length. Catheter 12 further includes a lumen 44. The diameter of the lumen 44 may vary and is selected to accommodate a desired flow rate and/or pressure from the intravenous fluid source. Catheter 12 may be from 14-26 gauge.

As shown in FIGS. 2 and 4, catheter 12 further includes a flexured portion 21. Flexured portion 21 is defined as the uninserted section of the catheter between the first end of the catheter adapter tip opening and the catheter insertion site 51 of the patient 52. The length is defined by the distance between flexured portion 21 of catheter 12 and catheter tip 31. The proximity of flexured portion 21 to the first end of the catheter adapter 18 makes the flexured portion prone to occlusion. This is because the first end of the catheter adapter exerts an upward force on flexured portion 21 when the catheter 12 is moved independent of and relative to the generally horizontal plane of the catheter adapter. The length of uninserted catheter, and therefore the point of maximum insertion, is selected such that a sufficient length of catheter remains uninserted. This allows the flexured portion of the catheter to gently bend in making the transition from the catheter adapter to the insertion site thereby preventing an occlusion due to over-insertion of the catheter.

In one or more embodiments, catheter 12 may be made from a biomaterial designed to reduce mechanical phlebitis and infiltration. In one or more embodiments, catheter 12 may be made from polyurethane. In a specific embodiment, the biomaterial may be a polyurethane that softens up to 70% in the vascular vein or artery to allow for increased patient comfort while providing kink resistance and improving catheter dwell time.

Catheter 12 further includes a catheter tip 31. Catheter tip 31 includes a catheter opening 46 selected to provide clearance for introducer needle 36. Introducer needle 36 extends coaxially through a catheter of the catheter adapter. The diameter of the catheter opening 46 is selected to provide minimal tolerance between the outer surface of introducer needle 36 and the inner surface of catheter opening 46. As such, catheter tip 31 may provide a sufficiently sized access route into a patient's vein 64. The introducer needle 36 may further include a bevel on the distal tip. The bevel of the needle may be oriented in an asymmetrical orientation in relation to the conical relief or the internal curvature at surface 35 of the lower portion of the catheter adapter tip opening 34.

In one or more embodiments, the lower portion of adapter tip 32 includes the tip having the distal opening having the circumference through which the catheter extends, and wherein a catheter exiting the distal opening is flexibly supported by the internal curvature at surface 35 of the lower portion of the catheter adapter tip opening 34. FIGS. 3-5 show the area of support of the integrally molded tip catheter transition kink resistant feature. The catheter adapter tip opening 34 includes a surface 35 having an internal curvature defining a tapered region in the lower portion but not the upper portion, wherein the tapered region supports the flexured portion of the catheter to provide an angle of insertion for the catheter without restricting a flow through the catheter, the tapered region being less than the overall length. After insertion of the catheter, the tapered region provides transitional support at an angle of insertion for the catheter without restricting flow through the catheter. The catheter adapter tip opening 34 may include a steep or gradual insertion angle. FIG. 4 shows the area of support of the integrally molded tip catheter transition kink resistant feature. The internal curvature defining a tapered region in the lower portion eliminates the non-supported, abrupt change in direction current catheters experience upon exiting the catheter adapter 20, thereby minimizing the localized stress on the catheter 12 and therefore minimizing the chance of collapsing and kinking the catheter and occluding the fluid flow.

In one more embodiments, the overall length L of the catheter adapter is substantially equivalent at the upper portion and the lower portion, and the catheter adapter tip opening 34 has an internal curvature defining a tapered region, and wherein the internal curvature of the lower portion of the catheter adapter tip opening 34 defines a chamfer.

In one or more embodiments, catheter adapter 18 is generally tubular. A portion of the catheter is housed within the internal cavity of the catheter adapter. The catheter 12 is incorporated into a catheter adapter 18 using industry standard methods. Catheter adapter 20 further includes a body 48 extending between the proximal end 24 and the distal end 22. In one or more embodiments, the catheter is fixedly attached to the catheter adapter in a fluid-tight manner. As such, a fluid from the intravenous fluid source may flow through the lumen 44 and into the catheter 12 without interruption. The distal end 22 of the catheter adapter is generally tapered and includes catheter adapter tip opening 34 through which the catheter 12 extends. The proximal end 24 generally includes an access port 54 for accessing lumen 44 of the catheter. Access port 54 may be a dual access port that provides multiple options for administration of fluid and medications.

Additional features of the catheter adapter may include a lateral access port 56 extending from and being in fluid communication with the catheter adapter. An extension tube 60 may be attached to the lateral access port 56 to permit controlled flashback. The lateral access port 56 may be connected to a section of extension tube 60 for establishing fluid communication between an intravenous fluid source and the internal cavity 26 of the catheter adapter or lumen 44 of the catheter.

In one or more embodiments, extension tube 60 extends from the lateral access port or proximal end of the catheter adapter to establish a fluid communication with the internal cavity of the adapter. The extension tubing could extend in line with or laterally with the body of the catheter adapter. The extension tubing may be built-in to reduce contamination and mechanical phlebitis by eliminating manipulation at the insertion site. The extension tubing may be-compatible with high pressure injection. The extension tubing provides continuous confirmation of vessel access during advancement of the catheter into the patient vein.

Catheter adapter 18 may also be configured to house introducer needle 36 for inserting the catheter 12 into a patient. In one or more embodiments, introducer needle 36 includes a notch 58 to provide immediate confirmation of vessel entry at the point of insertion to improve first-stick success.

As shown in FIGS. 1 and 7, one or more embodiments of the catheter adapter 20 may include wing element 62. Wing element 62 is attached to the catheter adapter 20 and extends radially outward from the catheter adapter 20.

In one or more embodiments, wing element 62 includes a first wing member 68 extending from one side of the catheter adapter 18. In yet another embodiment, the wing element includes a first wing member 68 extending in a first direction from the one side of the catheter adapter 18 and a second wing member 70 extending in a direction opposite to the first direction. In one or more embodiments, the first wing member and second wing member 70 are integrally molded. However, the first wing member and second wing member 70 need not be integrally molded, and each of these components can be separately molded from the same or different materials. In addition, while first wing member 68 and second wing member 70 are shown as being a contiguous piece to form the wing element 62, first wing member 68 and second wing member 70 can be separate pieces. In addition, according to one or more embodiments, the wing element can comprise a single wing member, either first wing member 68 or second wing member 70. First wing member 68 and second wing member 70 provide increased catheter stability and therefore increase dwell time.

In one or more embodiments, at least a portion of the catheter adapter 18 is made from a first material and at least a portion of the adapter tip 32 is made from a second material that is more flexible than the first material. In a specific embodiment at least a majority of the catheter adapter 18 is made from a first material and at least a portion of the adapter tip 32 is made from a second material that is more flexible than the first material. As used herein, "majority" means greater than 50% of the volume of catheter adapter, excluding the wing element. To determine the amount of the first material, the overall volume of the first material is determined, the overall volume of the second material excluding the wing element is determined, and the total volume of the catheter adapter is determined by adding the volume of the first material and the volume of the second material excluding the wing element. The percent of the first material is determined by dividing the volume of the first material divided by the total volume of the catheter adapter.

In one or more embodiments, the catheter adapter, excluding the wing element and catheter, may be made from a rigid polymeric material selected from one or more of a polyester, co-polyester, polycarbonate, polyethylene, polystyrene or polypropylene. In one or more embodiments, first wing member 68 and second wing member 70 may be made from a soft, flexible polymeric material selected from one or more of a thermoplastic elastomer (TPE), thermoplastic polyurethane (TPU), thermoplastic vulcanizate elastomer (TPV), olefin block copolymers (OBC), polyisoprene, or silicone. In one or more embodiments, the second material has a durometer value in the range of 30 Shore A to 90 Shore D, with a preferred range of ~50 to 90 Shore A. Durometer hardness may be determined under test method ASTM D2240.

Referring now to FIG. 2, catheter adapter 18 is illustrated in a generally horizontal orientation. In use, the catheter adapter 18 is secured to a patient and the catheter tip 31 is inserted into the patient's vascular system. The catheter 12 is positioned and inserted within the patient's vascular system at a determined insertion angle 53. Insertion angle 53 is defined by the exit angle of the catheter at the catheter adapter tip opening 34 of the adapter when the catheter tubing is biased downward against the bottom curved surface of the ID of the catheter adapter. The insertion angle 53 may include any angle necessary to introduce the catheter into the patient's vascular system. For example, an insertion angle 53 may be selected within the range of 1° to 60°, with a preferable range of angle of insertion from 15° to 45°.

Following insertion of the catheter 12, the flexured portion 21 of the catheter is bent in a general arch shape to accommodate the transition of the catheter 12 from the catheter adapter 20 to the catheter insertion site 51. This feature also allows for a steeper insertion angle which can be useful for subcutaneous injection as it supports the catheter as it is secured flat against the skin after a steep insertion.

Upon insertion of the catheter into the insertion site, the catheter experiences higher leverage forces. Thus, the catheter acts as a lever and the rigid first end of the catheter adapter acts as a fulcrum exerting an upward force on the catheter. As the catheter is inserted further into the insertion site, the upward force of the catheter is dissipated by the internal curvature of the catheter adapter tip opening 34 which defines a tapered region in the lower portion with the catheter to prevent kinking and occlusion of the catheter, therefore, maintaining patency and flow rates throughout the life of the device. This is particularly useful in cases of drawing blood from an indwelling vascular access device including peripheral intravenous catheters (PIVC), peripherally inserted central catheter (PICC) or central venous catheter (CVC).

In one or more embodiments, the catheter adapter tip opening is chamfered such that the tolerance between the distal end of the catheter adapter and the flexured portion of the catheter is increased. Thus, the flexured portion of the catheter may bend more sharply before the catheter contacts the catheter adapter tip opening resulting in an occlusion. In one embodiment, the catheter adapter tip opening is chamfered at an angle which is less than 90° relative to the generally horizontal plane. The chamfered opening permits a greater length of catheter to be inserted before an occlusion occurs due to the delayed contact of the tip opening and the catheter. Therefore, as the flexured portion of the catheter is further inserted into the patient, the flexured portion is allowed to bend to a greater degree before contacting and pivoting on the tip opening resulting in an occlusion of the catheter at the flexured portion.

The degree of curvature at surface 35 is selected to support the flexured portion of the catheter in maintaining an insertion angle within the desired range. In this embodiment, the flexured portion 21 of the catheter is bent over and along the contour of the rounded, curved or chamfered lower portion of the catheter adapter tip opening 34. The flexured portion is supported by the lower portion of the catheter adapter tip opening 34 in maintaining the necessary degree of curvature for the catheter so as to avoid an occlusion and maintain the optimal degree of insertion. The rounded, curved or chamfered opening minimizes the fulcrum function of the distal end of the catheter adapter on the flexured portion of the catheter such that the catheter may be maximally inserted into the patient with minimal upward force of the distal end of the catheter. This minimizes the likelihood of occlusion. The flexured portion may form a gentle arch thus preventing an occlusion of the catheter 12 due to over-insertion of the catheter 12. The length of uninserted catheter, and therefore the point of maximum insertion is selected such that a sufficient length of catheter 12 remains uninserted. The internal curvature of the catheter adapter tip opening 34 in the lower portion provides structural support for the catheter's direction and angular change from the adapter into the patient's body, thereby eliminating the abrupt change in direction that current catheters experience upon exiting the catheter adapter. Therefore, the internal curvature of the catheter adapter tip opening 34 in the lower portion minimizes the localized stress and chance of collapsing and kinking. After insertion of the catheter, the tapered region provides transitional support at an angle of insertion for the catheter without restricting flow through the catheter. This allows the flexured portion of the catheter 12 to gently bend in making the transition from the catheter adapter to the insertion site thereby preventing an occlusion of the catheter.

The shape and profile of the internal curvature of the catheter adapter tip opening 34 can be optimized for each individual size catheter, for a given insertion depth d, to reduce localized stress and provide structural support for the catheter's angular directional change. In the embodiment illustrated above in FIG. 5, the curvature extends from the opposite cross sectional quadrants of the catheter adapter inner diameter and transitions downward in the direction of the patient. The upper portion 28 of the catheter adapter tip opening is without curvature and provides upward bending support during the catheter insertions process. Upon insertion and removal of the insertion needle, the internal curvature of the catheter adapter tip opening 34 of the lower portion allows the adapter and catheter, having been inserted at some angle, to be laid flat against the patient's skin without undue localized stress and abrupt directional change. As shown in FIG. 5, the internal curvature of the catheter adapter tip opening 34 in the lower portion decreases the impact of an abrupt angle change when the catheter (shown in phantom) is secured to the patient after a steep insertion angle, reducing the risk of the catheter kinking at the exit of the catheter adapter nose.

The catheter adapter according to one or more embodiments can provide a variety of cross sectional transitions at the catheter adapter tip opening 34. The cross-sectional transition can be varied to provide an intended curved support for the catheter depending on the potential direction of bending of the catheter. This cross-sectional transition feature according to one or more embodiments reduces the risk of the catheter tube kinking and restricting flow through the device to the patient during an infusion procedure, as well as from the patient through the device for drawing blood and while checking patency. The examples shown in FIGS. 6A, 6B and 6C curvature is only on the bottom portion of the inner diameter, however, many other alternatives exist, including a full round inner diameter expansion if the curvature (e.g., trumpet shaped), or any number of rotationally or axially variable transitions. FIGS. 6A, 6B and 6C illustrate three non-limiting examples of cross-sectional profiles of catheter tips, wherein the view is of the catheter adapter tip at the catheter exit opening. FIG. 6A shows an adapter first modified tip opening 34a having a chamfered surface 35a at the lower portion. FIG. 6B shows a second modified adapter tip opening 34b having a curved surface 35b at the lower portion. FIG. 6C shows a third modified adapter tip opening 34c having a rounded surface 35c at the lower portion.

In one or more embodiments, the catheter adapter includes a flexible, kink resistant extension extending from the catheter adapter tip opening to provide support for the catheter.

The catheter adapter 20 described with respect to FIGS. 1-6 can be used as part of a vascular access device described with respect to FIG. 7.

As shown in FIG. 7, the catheter adapter 18 may be part of a vascular access device 10, with additional components in fluid communication with the catheter adapter 18. As shown in FIG. 7, the lateral access port 56 may be connected to a section of extension tube 60 for establishing fluid communication between an intravenous fluid source and the internal cavity 26 of the catheter adapter or lumen 44 of the catheter. In one or more embodiments, the extension tube 60 extends in line with or laterally with the body of the catheter adapter. In one or more embodiments, the extension tube 60 is built-in to reduce contamination and mechanical phlebitis by eliminating manipulation at the insertion site. In one or more embodiments, the extension tube 60 is compatible with high pressure injection. In one or more embodiments, the extension tube 60 provides continuous confirmation of vessel access during advancement of the catheter into the patient's vein 64.

In one or more embodiments, needle hub assembly 50 is assembled with the catheter adapter by inserting the needle into the lumen 44 of the catheter 12. The needle hub assembly is shown as including finger grips 84 positioned at the sides of the needle hub assembly 50 to facilitate various insertion techniques. In one or more embodiments, bumps may be present on the finger grip to indicate where to the user may grip the device for needle removal. In one or more embodiments, a thumb pad 85, having a gently convex surface, is provided at the proximal end of the needle hub assembly 50. A flange 86, having a gently convex surface, is provided at the proximal end of the hub assembly to provide a finger pad.

First wing members 68, second wing member 70, thumb pad 85 and flange 86 may be utilized by the user during insertion, permitting the user to elect which insertion technique to employ.

In one or more embodiments, the needle hub assembly 50 includes a needle shield 80. The needle shield may be a design adapted to secure the tip of the needle within the shield after use. In one or more embodiments, the needle shield may be activated passively to ensure compliance with compromising user technique. The needle tip is completely covered by the needle shield in a fixed position. In one or more embodiments, a ferrule, crimp or other structure may be included near the tip for engagement with a needle shield in certain applications.

A push tab 81 may be provided to facilitate catheter advancement during insertion. The push tab also allows for one-handed or two-handed advancement. In one or more embodiments, the push tab is removed with the needle shield. A clamp 82 may also be included on the extension tubing to prevent blood flow when replacing the access port.

The proximal end of the introducer needle may be crimped to provide a fluid-tight seal around the proximal end of the introducer needle. The introducer needle may be glued or mechanical interlocks may be formed to secure the introducer needle to the hub.

In one or more embodiments, the vascular access device 10 further includes a first luer access 72 and a second luer access 73 in fluid communication with the extension tube 60, a blood control split septum 74 associated with the first luer access 72, and an air vent 76 associated with the second luer access 73. Split septum 74 allows for a reduction in catheter-related bloodstream infection (CRBSI) while providing unrestricted flow and a straight fluid path and functions as a blood control septum. In one or more embodiments, the split septum 74 may be located in an internal cavity of the catheter adapter or on the distal end of the catheter adapter. In yet another embodiment, the split septum 74 may be located on a distal end of the extension tube 60. The air vent 76 allows air to escape from the system during insertion, providing continuous confirmation of vascular access while preventing leakage of blood from the system during insertion. In one or more embodiments, the air vent 76 may be at the distal end of extension tube 60.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments,"

"in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A vascular access device comprising:
    a catheter including a flexured portion; and
    a catheter adapter having a distal end, a proximal end, an overall length extending from the distal end to the proximal end, an internal cavity, an upper portion, a lower portion and a distal tip having a catheter adapter tip opening having a circumference and through which the catheter extends, wherein the overall length is substantially equivalent at the upper portion and the lower portion, the upper portion of the catheter adapter tip opening does not include an internal curvature extending from the distal tip, the upper portion of the adapter in contact with the catheter having a substantially straight surface to maintain rigidity, and the catheter adapter tip opening having an internal curvature defining a tapered region in the lower portion, wherein the tapered region supports the flexured portion of the catheter to provide an angle of insertion for the catheter without restricting a flow through the catheter, the tapered region being less than the overall length,
    wherein the internal curvature in the lower portion of the adapter extends across a portion of a circumference of catheter adapter tip opening and defines an arc forming an angle in a range greater than 90° to 270°.

2. The vascular access device of claim 1, wherein the internal curvature of the lower portion of the catheter adapter tip opening defines a chamfer.

3. The vascular access device of claim 1, wherein the internal curvature of the lower portion of the catheter adapter tip opening is rounded.

4. The vascular access device of claim 1, wherein the internal curvature of the lower portion of the catheter adapter tip opening is trumpet shaped.

5. The vascular access device of claim 1, wherein the lower portion of the catheter adapter tip opening defines a radius at the distal tip that incrementally decreases moving away from the distal tip.

6. The vascular access device of claim 1, wherein the vascular access device is selected from a group including a central venous catheter, a peripherally inserted central catheter, a peripheral intravenous cannula, an arterial catheter, and a mid-line catheter.

7. The vascular access device of claim 1, wherein a portion of the catheter is housed within the internal cavity of the catheter adapter.

8. The vascular access device of claim 1, wherein the catheter is fixedly attached to the catheter adapter.

9. The vascular access device of claim 1, wherein the angle of insertion is within a range of about 1° to about 60°.

10. The vascular access device of claim 9, wherein the angle of insertion is about 15-45°.

11. The vascular access device of claim 1, wherein a radius of the upper portion is asymmetrical in relation to the radius of the lower portion.

12. The vascular access device of claim 1, wherein the upper portion of the catheter adapter is oriented tangentially to the catheter.

13. The vascular access device of claim 1 further comprising an introducer needle in the internal cavity, the needle having a distal end a proximal end and a needle hub connected to the proximal end of the introducer needle.

14. The vascular access device of claim 13, further comprising an extension tube extending from the catheter adapter and in fluid communication with the internal cavity of the catheter adapter.

15. The vascular access device of claim 14, further comprising at least one of a luer access, a blood control septum, an air vent and a notch in the introducer needle.

16. The vascular access device of claim 1, further comprising a wing element extending radially outward from the catheter adapter.

17. The vascular access device of claim 16, wherein the wing element comprises a first wing member extending from one side of the catheter adapter.

18. The vascular access device of claim 17, wherein the wing element comprises a second wing member extending opposite the one side of the catheter adapter.

19. The vascular access device of claim 1, wherein at least a portion of the catheter adapter is made from a first material and at least a portion of the distal tip is made from a second material that is more flexible than the first material.

20. The vascular access device of claim 19, wherein at least a majority of the catheter adapter is made from a first material and at least a portion of the distal tip is made from a second material that is more flexible than the first material.

21. The vascular access device of claim 1, wherein the distal tip includes a flexible, kink resistant extension extending from the catheter adapter tip opening to provide support for the catheter.

22. The vascular access device of claim 20, further comprising a wing element extending radially outward from the catheter adapter.

23. The vascular access device of claim 21, wherein the wing element comprises a first wing member extending from one side of the catheter adapter.

24. The vascular access device of claim 22, wherein the wing element comprises a second wing member extending opposite the one side of the catheter adapter.

25. The vascular access device of claim 1, wherein the catheter is made from polyurethane.

26. The vascular access device of claim 14, wherein the tapered region provides conical relief to the catheter.

27. The vascular access device of claim 25, wherein the needle further includes a bevel on the distal tip and the bevel of the needle is oriented in an asymmetrical orientation in relation to the conical relief.

28. The vascular access device of claim 1, wherein the upper portion is absent a catheter adapter tip opening having an internal curvature defining a tapered region.

29. An apparatus for preventing a restricted flow within a catheter comprising:
    a catheter adapter having a distal end, a proximal end, an overall length extending from the distal end to the proximal end, an internal cavity, an upper portion, a lower portion and a distal tip having a catheter adapter tip opening through which a catheter including a flexured portion extends, wherein the overall length is substantially equivalent at the upper portion and the lower portion, the upper portion is absent a catheter adapter tip opening having an internal curvature, the lower portion of the adapter has a curved surface defining a tapered region to support the flexured portion of the catheter at a desired angle of insertion into a patient and to prevent kinking of the catheter, the upper portion of the adapter in contact with the catheter having a substantially straight surface and constant thickness to maintain rigidity of the catheter during insertion of the catheter into a patient, wherein the internal curvature in the lower portion of the adapter extends across a portion of a circumference of catheter adapter tip opening and defines an arc forming an angle in a range greater than 90° to 270°.

30. The apparatus of claim 29, wherein the lower portion of the catheter adapter tip opening defines in cross section a semicircular arc.

31. The apparatus of claim 30, wherein the lower portion of the catheter adapter tip opening defines in cross section a partial ellipse.

* * * * *